US00PP31423P3

(12) United States Plant Patent
Valin

(10) Patent No.: US PP31,423 P3
(45) Date of Patent: Jan. 28, 2020

(54) ***HELIANTHUS* PLANT NAMED 'TMSNBLEV01'**

(50) Latin Name: ***Helianthus* x *hybridus***
Varietal Denomination: TMSNBLEV01

(71) Applicant: Branded Garden Products Ltd, South Hampton (GB)

(72) Inventor: Charles Valin, Harkstead (GB)

( * ) Notice: Subject to any disclaimer, the term of this patent is extended or adjusted under 35 U.S.C. 154(b) by 0 days.

(21) Appl. No.: 16/501,234

(22) Filed: Mar. 8, 2019

(65) Prior Publication Data

US 2019/0357411 P1 Nov. 21, 2019

Related U.S. Application Data

(60) Provisional application No. 62/762,737, filed on May 16, 2018.

(51) Int. Cl.
*A01H 5/02* (2018.01)
*A01H 6/14* (2018.01)

(52) U.S. Cl.
USPC ..... Plt./436

(58) Field of Classification Search
USPC ..... Plt./263.1, 436
See application file for complete search history.

*Primary Examiner* — Susan McCormick Ewoldt
*Assistant Examiner* — Karen M Redden
(74) *Attorney, Agent, or Firm* — Cassandra Bright

(57) ABSTRACT

A *Helianthus* plant named 'TMSNBLEV01' is disclosed, characterized by bright yellow fully double flowers composed of only ray florets. Plants have an attractive spreading habit and flower prolifically. The flowering period is exceptionally long, from around early Spring until mid to late Fall. Plants are useful for outdoor ornamental purposes, normally produced as an outdoor garden or container plant.

2 Drawing Sheets

Genus and species: *Helianthus* x *hybridus*.
Variety denomination: 'TMSNBLEV01'.

BACKGROUND OF THE INVENTION

'TMSNBLEV01' is a product of a breeding and selection program for ornamental *Helianthus* varieties to be vegetatively propagated. The new plant of the present invention comprises a new and distinct cultivar of *Helianthus* plant.

'TMSNBLEV01' is a seedling resulting from the crossing of the seed parent, an unpatented proprietary *Helianthus hybridus* referred to as 'HE13026' with the pollen parent, an unpatented proprietary *Helianthus hybridus* referred to as 'HE13002'. The crossing resulting in this new variety was conducted in July 2014 in Suffolk, UK. The selection of the new variety was made in July 2015, by the inventor at a research greenhouse located in Suffolk, UK.

'TMSNBLEV01' was first asexually reproduced by terminal vegetative cuttings at a greenhouse in Suffolk UK, August 2015 and has been asexually reproduced over an approximately three-year period. The new cultivar has been found to retain its distinctive characteristics through successive asexual propagations.

SUMMARY OF THE INVENTION

The following are the most outstanding and distinguishing characteristics of the new cultivar when grown under normal horticultural practices in Suffolk, UK:

1. Compact basal multi-branching habit.
2. Medium sized (12 cm) bi-color inflorescence colored yellow with a brown center.
3. Exceptionally long continuous blooming. Non-stop blooming May to first frosts, due to day length neutral quality.

4. Sterile flowers.
5. Heat tolerant.
6. Suitability for vegetative propagation

COMPARISON WITH PARENT VARIETIES

Plants of the new cultivar 'TMSNBLEV01' are similar to plants of the seed parent in most horticultural characteristics. The new variety however, differs in the following:

1. Blooming period of the new variety is May until first frost, the seed parent blooming period is July and August.
2. The new variety is totally sterile, the seed parent is pollenless but seed fertile.
3. The seed parent does not tolerate heat as well as the new variety.
4. Plants of the new variety are compact with multiple branches, plants of the seed parent are erect.

Plants of the new cultivar 'TMSNBLEV01' are similar to plants of the pollen parent in most horticultural characteristics. The new variety however, differs in the following:

1. Blooming period of the new variety is May until first frost, the pollen parent blooming period is June to October.
2. The new variety is totally sterile, the pollen parent is fully fertile.
3. The pollen parent has small entirely yellow inflorescence, the new variety has medium sized bi-color inflorescence.
4. Plants of the new variety are compact with multiple branches, plants of the seed parent are erect.

COMPARISON WITH COMMERCIAL CULTIVARS

'TMSNBLEV01' can be compared to the commercial variety 'Double Whammy', U.S. Plant Pat. No. 25,494.

Plants of the two varieties are similar in most horticultural characteristics, however, 'TMSNBLEV01' differs in the following:

1. Flowers of the new variety are medium sized and bi-color, flowers of this comparator are a single golden yellow color.
2. Blooming period of the new variety is May until first frost, the blooming period of this comparator is August to October.
3. Plants of the new variety are well branched and compact, plants of this comparator are tall and upright.
4. Flowers of the new variety are single, flowers of this comparator are double.
5. Flowers of the new variety are fully sterile, flowers of this comparator are fully fertile.

'TMSNBLEV01' can be compared to the commercial variety 'Table Mountain', (U.S. 2007/0050874—abandoned). Plants of the two varieties are similar in most horticultural characteristics, however, 'TMSNBLEV01' differs in the following:

1. Flowers of the new variety are medium sized and bi-color, flowers of this comparator are small and a single deep yellow color.
2. Blooming period of the new variety is May until first frost, the blooming period of this comparator is August to September.
3. Plants of the new variety are well branched and compact, plants of this comparator are upright.
4. Flowers of the new variety are fully sterile, flowers of this comparator are fully fertile.

DESCRIPTION OF THE PHOTOGRAPHS

The present invention of a new and distinct variety of *Helianthus* is shown in the accompanying photographs, the colors being as nearly true as possible with color photographs of this type.

DESCRIPTION OF THE INVENTION

Figure 1:
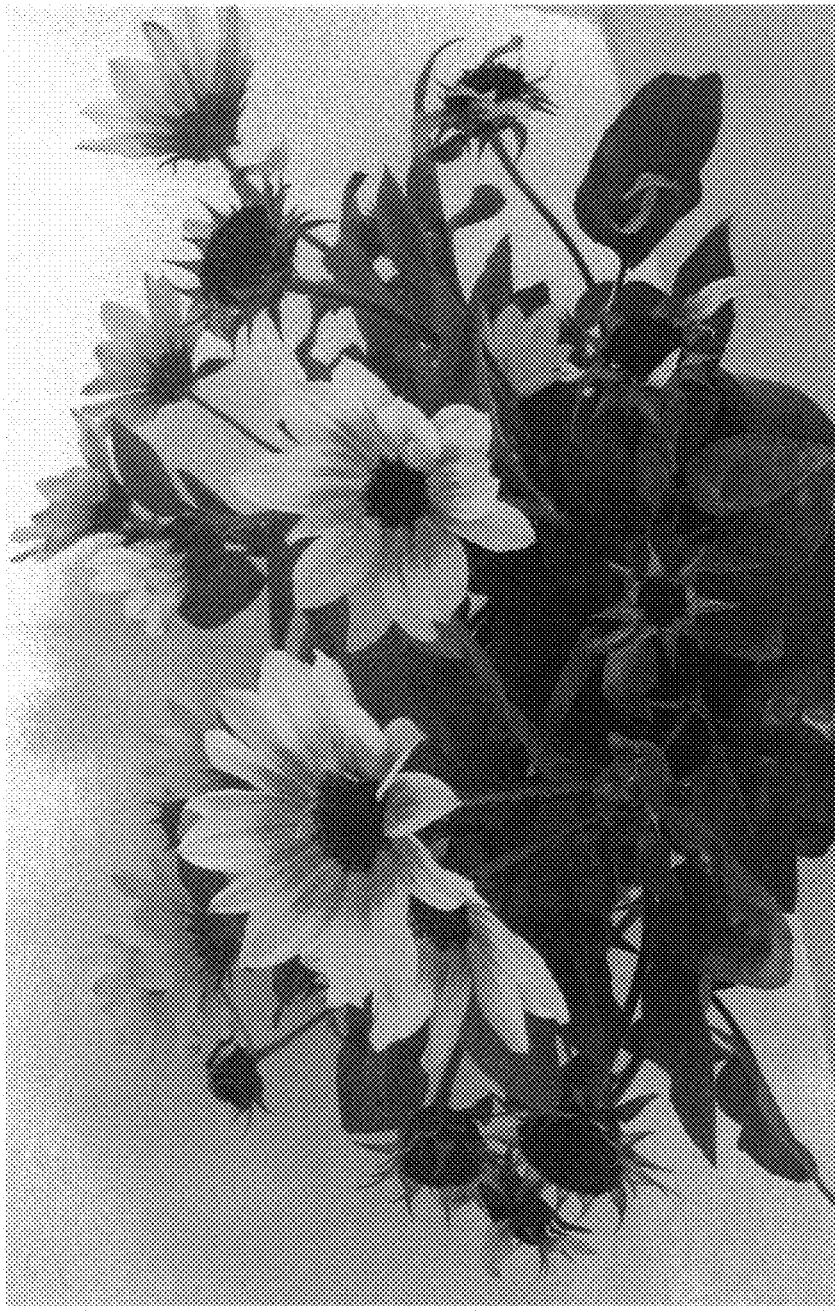
FIG. 1 illustrates a plant of approximately 6 months in a 1 gallon pot
Figure 2:
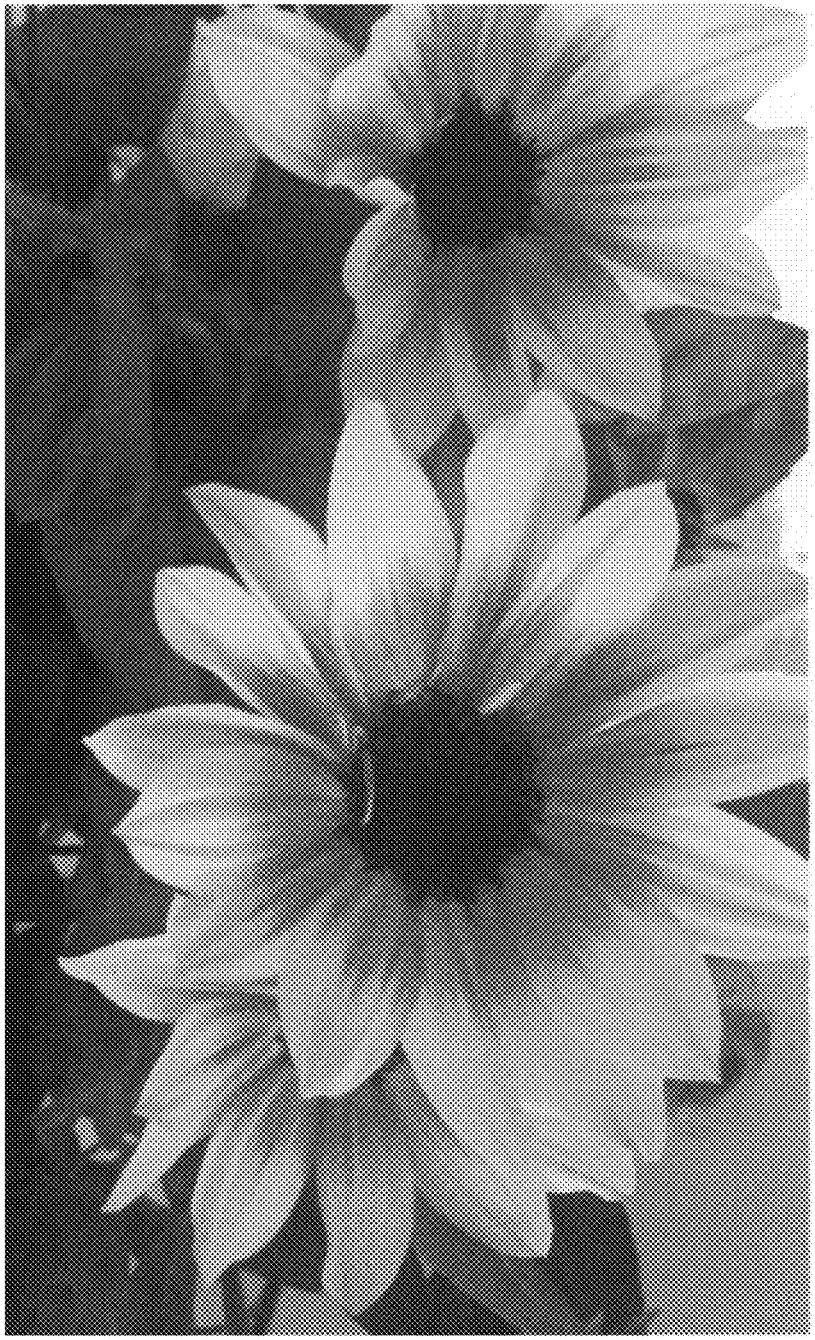
FIG. 2 illustrates a close up of the inflorescence.

This new variety of *Helianthus* is of the botanical classification *Helianthus hybridus*. The observations and measurements were gathered from plants grown outdoors in San Juan Bautista, Calif. under natural light, natural day length and temperatures. Measurements were taken during April.

The following is a description of the plant and characteristics that distinguish 'TMSNBLEV01' as a new and distinct variety. The color designations are taken from the plant itself. Accordingly, any discrepancies between the color designations and the colors depicted in the photographs are due to photographic tolerances. The color chart used in this description is The Royal Horticultural Society color chart, edition 2007.

DETAILED BOTANICAL DESCRIPTION

Classification:

*Botanical.—Helianthus hybridus.*

*Denomination.*—'TMSNBLEV01'.

PROPAGATION

Typical method: Terminal vegetative cuttings.

Root description: Fine and fibrous brown to tan roots, not accurately measured with R.H.S. chart.

PLANT

Shape: Upright and outward.

Growth habit: Herbaceous perennial.

Growth rate: Moderately vigorous.

Height: 21 cm.

Width: 30 cm.

Branches/stems:

*Color.*—Near RHS Yellow-Green 144A, flushed Greyed-Purple 187A.

*Strength.*—Moderately strong.

*Length of lateral branch.*—Average 5 to 15 cm.

*Diameter of lateral branch.*—Average 8 mm.

*Aspect.*—Approximately 15 to 35 degree angle.

*Average number of lateral branches.*—6 to 8 main stems, each with 3 to 5 lateral branches.

*Texture.*—Hirsute. Moderate density of hairs. Hairs about 2 mm long, colored near White 155A.

*Internode length.*—Average range 2.8 to 3.7 cm.

FOLIAGE

Arrangement: Sub-opposite.

Average length: Approximately 9 to 10 cm, including petiole.

Average width: Approximately 3.5 to 4.5 cm.

Shape of blade: Slightly asymmetrical ovate.

Apex: Acute.

Base: Rounded and somewhat oblique.

Attachment: Stalked.

Margin: Shallow dentate.

Texture of top surface: Hirsute.

Texture of bottom surface: Hirsute.

Appearance top surface: Matte.

Appearance bottom surface: Matte.

Color:

*Young foliage upper side.*—Near Green 137A.

*Young foliage under side.*—Near Green 137B.

*Mature foliage upper side.*—Near Yellow-Green 147A.

*Mature foliage under side.*—Near Yellow-Green 147B.

Venation:

*Type.*—Pinnate.

*Venation color upper side.*—Lateral veins near Green 137A. Apical section of mid-vein near Yellow-Green 144C. Lower mid-vein near Greyed-Purple N186A.

*Venation color under side.*—Near Yellow-Green 146D. Lowermost mid-vein flushed Greyed-Purple N186A.

Petiole:

*Length.*—Average range 2.0 to 3.0 cm.

*Diameter.*—2 to 3 mm.

*Texture.*—Hirsute.

*Color.*—Near Greyed-Purple N186B.

FLOWER

Bloom period: May until first frost in Suffolk, UK.

Bud:

*Bud shape.*—Broad conical.

*Bud length.*—Approximately 2.0 cm.

*Bud diameter.*—Approximately 1.5 cm.

*Bud color*.—Main color near Green 137A, turning Yellow 12A towards apex.

Inflorescence:

*Form*.—Terminal capitulum.

Inflorescence:

*Quantity per plant*.—About 4 to 8 buds and flowers per lateral stem.

*Diameter*.—Average 12 cm.

*Depth*.—Approximately 5 cm.

*Persistence*.—Ray florets self-cleaning, disc florets persistent.

Ray florets:

*Number of ray florets*.—Average range 14 to 20.

*Arrangement*.—Rotate, in a semi-double whorl.

*Length*.—Approximately 5 cm.

*Width*.—Approximately 1.4 cm.

*Apex shape*.—Acute to nearly mucronate.

*Base*.—Tapered.

*Margin*.—Entire.

*Texture*.—Smooth all surfaces.

*Aspect*.—Overall slightly reflexed down, margins upwardly curving. Linear puckered ridges.

*Appearance*.—Matte upper and lower surfaces.

Color:

Ray florets:

*Upper surface at first opening*.—Near Yellow 12A, lower approximate ⅓ near Greyed-Orange 172A.

*Under surface at first opening*.—Near Yellow 12B, lower approximate ⅓ flushed near Greyed-Orange 175D.

*Upper surface at maturity*.—Near Yellow 12A, lower approximate ⅓ near Greyed-Orange 175B.

*Under surface at maturity*.—Near Yellow 12B, lower approximate ⅓ flushed near Greyed-Orange 175C.

Disc florets:

*Number of disc florets*.—Average range 40 to 60.

*Length*.—Approximately 7 mm.

*Width*.—Approximately 2 mm.

*Shape*.—Linear.

*Margin*.—Entire.

*Texture*.—Pubescent.

*Color*.—At first opening: Near Brown 200A. Lower section near Yellow-Green 145D. At maturity: Near Brown 200A. Lower section near Yellow-Green 145D. At fading: Near Brown 200A. Lower section near Yellow-Green 145D.

Fragrance: Faint, earthy scent.

Chaff:

*Quantity*.—Moderate.

*Shape*.—Linear to narrow deltate.

*Length*.—4 to 5 mm.

*Width*.—2 mm.

*Color*.—Immature: Near Yellow-Green 145D. Mature: Near Greyed-Purple N186A, base near Yellow-Green 145D.

Phyllaries/involucral bracts:

*Number*.—Average 24, in 2 or 3 whorls.

*Length*.—Average range 1.4 to 2.0 cm.

*Width*.—Approximately 6 mm.

*Texture*.—Upper and lower surfaces coarsely pubescent.

*Apex shape*.—Apiculate.

*Margin*.—Entire.

*Color*.—Upper surface: Apical section near Green 137A, lower section near Yellow-Green 145A. Lower surface: Apical section near Green 137A, lower section near Yellow-Green 144A.

Peduncle:

*Peduncle length*.—Average range 6 to 9 cm.

*Peduncle diameter*.—Approximately 3 mm.

*Aspect*.—Straight with occasional slight curvature.

*Color*.—Near Yellow-Green 146C, flushed Greyed-Purple N186B.

*Peduncle texture*.—Hirsute. Hairs 2 to 3 mm, colored near White 155D.

Receptacle:

*Height*.—Approximately 5 mm

*Diameter*.—Approximately 1.5 cm.

*Color*.—Near Yellow-Green 145C.

*Shape*.—Flattened.

REPRODUCTIVE ORGANS

Ray florets:

*Gynoecium*.—Pistil number: 1. Pistil length: Approx. 10 mm. Style length: Approx. 9 mm. Style color: Near Yellow 7D. Stigma shape: Linear. Stigma color: Near Yellow-Orange 21B.

*Androecium*.—Not present.

Disc florets:

*Androecium*.—Often mal-formed. Stamens: 2, most commonly. Style Length: About 4 mm. Anther shape: Linear. Anther length: Approximately 1 mm. Anther color: Near RHS Greyed-Purple N187D. Pollen quantity: Not observed.

*Gynoecium*.—Pistil number: 1, often mal-formed. Pistil shape: Linear. Pistil length: Approx. 3 mm. Style length: Approx. 2 mm. Style color: Near Yellow-Green 154B, flushed Greyed-Purple N187D. Stigma shape: Linear. Stigma color: Near Yellow-Green 154B, flushed Greyed-Purple N187D.

OTHER CHARACTERISTICS

Disease and pest resistance: Neither resistance nor susceptibility to additional normal diseases and pests of *Helianthus* has been observed.

Fruit/seed production: Plants sterile, seeds not produced.

What is claimed is:

1. A new and distinct variety of *Helianthus* plant named 'TMSNBLEV01' as described and shown herein.

* * * * *